United States Patent
D'Oro et al.

(10) Patent No.: US 11,197,826 B2
(45) Date of Patent: Dec. 14, 2021

(54) OIL-IN-WATER EMULSIONS INCLUDING RETINOIC ACID

(71) Applicant: NOVARTIS AG, Basel (CH)

(72) Inventors: Ugo D'Oro, Vienna (IT); Luis Brito, Cambridge, MA (US); Derek O'Hagan, Camridge, MA (US); Silvia Vendetti, Rome (IT)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/065,468

(22) PCT Filed: Dec. 21, 2016

(86) PCT No.: PCT/EP2016/082096
§ 371 (c)(1),
(2) Date: Jun. 22, 2018

(87) PCT Pub. No.: WO2017/108902
PCT Pub. Date: Jun. 29, 2017

(65) Prior Publication Data
US 2019/0083397 A1  Mar. 21, 2019

(30) Foreign Application Priority Data
Dec. 23, 2015 (EP) .................... 15202332

(51) Int. Cl.
| | | |
|---|---|---|
| *A61K 9/107* | (2006.01) |
| *A61K 39/39* | (2006.01) |
| *A61K 31/203* | (2006.01) |
| *A61K 9/00* | (2006.01) |
| *A61K 47/06* | (2006.01) |
| *A61K 45/06* | (2006.01) |
| *A61K 47/22* | (2006.01) |
| *A61K 39/00* | (2006.01) |
| *A61M 5/178* | (2006.01) |

(52) U.S. Cl.
CPC .......... *A61K 9/1075* (2013.01); *A61K 9/0019* (2013.01); *A61K 9/107* (2013.01); *A61K 31/203* (2013.01); *A61K 39/39* (2013.01); *A61K 45/06* (2013.01); *A61K 47/06* (2013.01); *A61K 47/22* (2013.01); *A61M 5/178* (2013.01); *A61K 2039/55511* (2013.01); *A61K 2039/55566* (2013.01)

(58) Field of Classification Search
None
See application file for complete search history.

(56) References Cited

U.S. PATENT DOCUMENTS

| | | | |
|---|---|---|---|
| 5,855,893 A | 1/1999 | Weinkauf et al. | |
| 5,980,917 A * | 11/1999 | Kang | A61K 8/0295 424/401 |
| 6,531,141 B1 | 3/2003 | Marvel | |
| 2010/0172941 A1 * | 7/2010 | Vajdy | A61K 39/145 424/283.1 |
| 2013/0129767 A1 * | 5/2013 | Tuikue Ndam | A61K 39/015 424/191.1 |
| 2013/0129786 A1 * | 5/2013 | Kraus | A61K 39/39 424/400 |
| 2014/0010835 A1 * | 1/2014 | Comstedt | A61K 39/02 424/190.1 |
| 2018/0296663 A1 * | 10/2018 | Hipp | A61K 39/12 |

FOREIGN PATENT DOCUMENTS

| | | |
|---|---|---|
| EP | 1001025 A2 | 6/2000 |
| JP | 9-501161 A | 2/1997 |
| JP | 2003-238389 A | 8/2003 |
| WO | 93/00085 A1 | 1/1993 |
| WO | 95/03781 A1 | 2/1995 |

OTHER PUBLICATIONS

Tan, X, et al., "Retinoic acid as an adjuvant to imprint mucosal homing properties to vaccine-induced T cells (39.32)", J. Immunology, pp. 1-4 (Year: 2009).*
Tan, et al., Retinoic Acid as a Vaccine Adjuvant Enhances CD8 T+ Cell Response and Mucosal Protection from Viral Challenge, Journal of Virology (Aug. 2011) vol. 85, No. 1, p. 8316-8327.
Mingke Yu, et al., A novel retinoic acid, catechin hydrate and mustard oil-based emulsion for enhanced cytokine and antibody responses against multiple strains of HIV-1 following mucosal and systemic vaccinations. Vaccine (Mar. 16, 2011) vol. 29, Issue 13, pp. 2429-2436.

* cited by examiner

*Primary Examiner* — Michael G. Hartley
*Assistant Examiner* — Lance W Rider
(74) *Attorney, Agent, or Firm* — Duane Morris LLP; Thomas J. Kowalski; Deborah L. Lu (57) ABSTRACT

Retinoic acid, or an analogue thereof, is delivered within an oil-in-water emulsion to provide an improved immunological adjuvant.

6 Claims, 1 Drawing Sheet

OIL-IN-WATER EMULSIONS INCLUDING RETINOIC ACID

CROSS-REFERENCE TO RELATED APPLICATIONS

This application in a national filing of International Application No.: PCT/EP2016/082096, filed Dec. 21, 2016, which claims the benefit of and priority to European Patent Application No.: 15202332.1 filed Dec. 23, 2015, which is hereby fully incorporated herein by reference.

TECHNICAL FIELD

This invention is in the field of delivering retinoic acid, and its analogues, as a vaccine adjuvant.

BACKGROUND ART

Retinoic acid is a vitamin A metabolite which is involved in immune regulation. It is believed to imprint a mucosal homing capacity on CD4+ and CD8+ T cells & B cells, and promotes the differentiation of IgA-producing cells. Antigen-presenting cells can produce retinoic acid which enables them to confer this mucosal homing capacity and thereby elicit mucosal and systemic immunity. Thus retinoic acid has been tested as a vaccine adjuvant in animals and humans, and has been given orally, intraperitoneally, or by subcutaneous implantation e.g. see references 1-5.

DISCLOSURE OF THE INVENTION

It is an object of the invention to provide further and improved methods of delivering retinoic acid, or an analogue thereof (collectively 'RA' hereafter), to exploit its immunological adjuvant activity. This object has been achieved by delivering RA within an oil-in-water emulsion. RA-containing oil-in-water emulsions have previously been disclosed [6], but for use as skin-care compositions, such as creams or lotions. Injectable oil-in-water emulsions are already known for use as vaccine adjuvants (e.g. the MF59 and AS03 products) and these can be enhanced by adding RA to them, possibly redirecting their immunological activity to provide improved mucosal immune responses, but without requiring a specific mucosal adjuvant or mucosal delivery.

Thus the invention provides an oil-in-water emulsion including RA, for use as an immunological adjuvant. Similarly, the invention provides a method for adjuvanting an immune response in a subject, comprising administering to the subject an oil-in-water emulsion including RA.

The invention provides an oil-in-water emulsion including RA, for use as a mucosal immunological adjuvant. Similarly, the invention provides a method for providing a mucosal immune response in a subject, comprising administering to the subject an oil-in-water emulsion including RA.

The invention also provides an injectable oil-in-water emulsion including RA.

The invention also provides an immunogenic composition comprising (i) an oil-in-water emulsion including RA and (ii) at least one immunogen.

The invention also provides a kit for preparing an immunogenic composition comprising (i) a first container including an oil-in-water emulsion comprising RA and (ii) a second container including at least one immunogen.

The invention also provides a syringe, optionally having an attached needle, wherein the syringe contains an oil-in-water emulsion comprising RA. The syringe's contents can also include at least one immunogen, so that a vaccine can be injected into a subject.

The invention also provides an oil-in-water emulsion including squalene and RA. This emulsion will typically also include at least one surfactant, as detailed below.

The invention also provides an oil-in-water emulsion including a tocopherol and RA. This emulsion will typically also include at least one surfactant, as detailed below.

The invention also provides an oil-in-water emulsion including RA, wherein the emulsion includes ≤20% by volume oil and/or ≤7% by volume surfactant.

The invention also provides an oil-in-water emulsion including RA, but not including one or more of: (i) oleic acid (ii) butylated hydroxytoluene; (iii) lecithin; (iv) medium-chain triglycerides; (v) soybean oil and/or (vi) cetyl palmitate.

The invention also provides a process for preparing an oil-in-water emulsion which includes RA, comprising a step of microfluidisation.

The invention also provides a process for preparing an oil-in-water emulsion, comprising a step of filtering an oil-in-water emulsion which includes RA using a filter having a pore size of 0.22 µm or lower. This process may involve steps of (i) preparing an oil-in-water emulsion which includes RA, then (ii) filtering the emulsion using a filter having a pore size of 0.22 µm or lower.

The invention also provides a process for preparing an oil-in-water emulsion, comprising a step of sterile-filtering an oil-in-water emulsion which includes RA. This process may involve steps of (i) preparing an oil-in-water emulsion which includes RA, then (ii) sterile-filtering the emulsion.

The invention also provides a process for preparing an immunogenic composition, comprising a step of mixing (i) an oil-in-water emulsion which includes RA, with (ii) a solution or suspension of an immunogen. The mixed composition is suitable for immunising subjects.

The invention also provides an oil/surfactant mixture including (i) squalene and/or a tocopherol and (ii) RA. This oil/surfactant mixture can be mixed with aqueous material to provide an oil-in-water emulsion adjuvant which includes RA.

Emulsions and immunogenic compositions of the invention can be used for raising immune responses as explained below.

Retinoic Acid and its Analogues

The invention concerns oil-in-water emulsions which include retinoic acid or an analogue thereof (collectively 'RA'). Retinoic acid is a vitamin A metabolite and it has various isomers, including all-trans ('ATRA'), 7-cis, 9-cis, 11-cis, 13-cis, 7,9-dicis, 7,11-dicis, 9,11-dicis, 9,13-dicis, and 11,13-dicis. Three of the isoforms have been used in approved medicines, namely alitretinoin (9-cis), isotretinoin (13-cis), and tretinoin (ATRA). Known analogues of retinoic acid include, but are not limited to, tazarotene, adapalene, tamibarotene, 5-(5,6,7,8-Tetrahydro-5,5,8,8-tetramethyl-2-anthracenyl)-3-thiophenecarboxylic acid, 4-(6-Hydroxy-7-tricyclo[3.3.1.13,7]dec-1-yl-2-naphthalenyl)benzoic acid, 4-[(5,6,7,8-Tetrahydro-5,5,8,8-tetra-methyl-2-naphthalenyl)carboxamido]benzoic acid, 4-[(E)-2-(5,6,7,8-Tetrahydro-5,5,8,8-tetra-methyl-2-naphthalenyl)-1-propenyl]]benzoic acid, 6-(4-Hydroxy-3-tricyclo[3.3.1.13,7]dec-1-ylphenyl)-2-naphthalenecarboxylic acid, 4-[(1E)-3-[3,5-bis(1,1-Dimethylethyl)phenyl]-3-oxo-1-propenyl]benzoic acid, 3-Fluoro-4-[[2-hydroxy-2-(5,5,8,8-tetramethyl-5,6,7,-tetra hydro-2-naphthalenyl)acetyl]amino]-benzoic acid, 4-[4-(2-Butoxyethoxy-)-5-methyl-2-thiazolyl]-2-fluorobenzoic acid, 4'-Octyl-[1,1'-biphenyl]-4-carboxylic acid, 4-[[(2,3-Dihydro-1,1,3,3-tetramethyl-2-oxo-1H-inden-5-yl)carbonyl]amino]benzoic acid, heterocyclic arotinoids [7], retinoids with bulky hydrophobic rings [8], 8-(2'-cyclohexen-1'-ylidene)-3,7-dimethyl-2,4,6-octatrienoic acids with various alkyl substituents at the 2' and 3' positions on the cyclohexene [9], and retinobenzoic acids [10] such as Am80 (4-[(5,6,7,8-Tetrahydro-5,5,8,8-tetramethyl-2-naphthyl)carbamoyl]benzoic acid). Thus a wide range of retinoic acid analogues are available in the art.

The invention can be used with any retinoic acid, or any retinoic acid analogue, which up-regulates CCR9 expression in antigen-specific T-lymphocytes. Most conveniently the invention uses ATRA, and any reference herein to 'RA' preferably utilises ATRA. In practice, however, it is difficult to retain pure ATRA due to isomerisation caused by light or in the presence of various thiol-containing compounds. Thus a composition may be prepared using ATRA but after storage it can include further retinoic acid isomers. Conversely, a composition may be prepared using a non-ATRA isomer but ATRA can arise during storage.

Retinoic acid is solid at room temperature and is generally supplied in crystalline form. It is sparingly soluble in water, but is soluble in oil, so in oil-in-water emulsions it will be almost exclusively located within the oil droplets (with some being present at the oil/water interface). To prepare an oil-in-water emulsion with RA, therefore, the general procedure is to prepare an oil phase (oil, RA, and optionally a surfactant with a low HLB) and an aqueous phase (optionally containing a surfactant with a high HLB), and then to mix these phases to prepare the emulsion. The oil phase can optionally include an organic solvent (in particular, a volatile organic solvent, such as dichloromethane) to assist in solubilising the RA. This solvent can be removed (e.g. by evaporation) before mixing the oil phase with the aqueous phase.

Because RA can deteriorate, particularly in the presence of water, it can be useful to keep the oil and aqueous phases separate from each other until the emulsion is needed e.g. to prepare the emulsion less than 24 hours before it will be used. Thus the invention provides an oil/surfactant mixture including (i) squalene and/or a tocopherol and (ii) RA. When desired this oil/surfactant mixture can be mixed with aqueous material to provide an oil-in-water emulsion which includes RA. Typically the surfactant in this oil/surfactant mixture will have a low HLB e.g. less than 10, and usually less than 5. The aqueous material can be water, but will usually include a buffer and may also include a surfactant (such as a surfactant having a HLB above 10).

RA dosing and pharmacokinetics following intravenous injection of ATRA and 13-cis retinoic acid have been studied both in rats at 10 mg/kg [11] and in monkeys at 0.25 or 0.0125 mg/kg [12]. For a plasma $C_{max}$ of around 3 ng/ml [1], a human dose of about 20 µg per injection is an aim. Thus an emulsion of the invention can include RA at a concentration between 2-200 µg/mL, considering a typical 0.5 ml dose. More generally, an emulsion of the invention can include RA at a concentration between 2 µg/mL to 2 mg/mL. Higher concentrations can be used for analogues which are less potent than ATRA; lower concentrations for analogues which are more potent.

Oil-in-Water Emulsions

The invention concerns oil-in-water emulsions which have immunological adjuvant activity i.e. the ability to enhance the immune response elicited in vivo against a co-administered immunogen. Such adjuvant-active emulsions include squalene-containing emulsions e.g. MF59 ([13]), AS03 [14], and AF03. According to the invention, the emulsions additionally include a RA component to enhance their performance e.g. in relation to mucosal immunity.

Various oil-in-water emulsion adjuvants are known, and they typically include at least one oil and at least one surfactant, with the oil(s) and surfactant(s) ideally being biodegradable (metabolisable) and biocompatible to facilitate in vivo usage.

The emulsion comprises one or more oils. Suitable oil(s) include those from, for example, an animal (such as fish) or a vegetable source. The oil is ideally biodegradable (metabolisable) and biocompatible. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. Fats and oils from mammalian milk are metabolisable and so may be used. The procedures for separation, purification, saponification and other means necessary for obtaining pure oils from animal sources are well known in the art.

Most fish contain metabolisable oils which may be readily recovered. For example, cod liver oil, shark liver oils, and whale oils such as spermaceti exemplify several of the fish oils which may be used herein. A number of branched chain oils are synthesized biochemically in 5-carbon isoprene units and are generally referred to as terpenoids. Preferred emulsions comprise squalene. Squalane, the saturated analog to squalene, can also be used. Fish oils, including squalene and squalane, are readily available from commercial sources or may be obtained by methods known in the art. Squalene is a branched, unsaturated terpenoid. It is typically purified from animal sources, such as shark (such as *Squalus acanthias*), but it is also possible to use squalene from non-animal sources, e.g., genetically-engineered yeasts [15] and vegetable oils such as olive oil [16,17]. Further possible sources include wheat germ oil, palm oil, amaranth seed (e.g., see [18]), and rice bran oil. It can be purified by distillation, e.g., as disclosed in [19]. As discussed in [20], when using shark-derived squalene it is preferred that polychlorinated biphenyls (PCBs) are present at a level of less than 661 pg PCBs per g squalene (TEQ). Full details of how to achieve a PCB level within this threshold are found in reference 20. Levels much lower than 661 pg/g can be achieved, even as low as ~2 pg/g. As well as having a low PCB content, it is useful to have a dioxin content less than 1 ng per gram of squalene, and preferably <1 pg/g (TEQ). Similarly, it is useful to have a furan content less than 1 ng per gram of squalene, and preferably <1 pg/g (TEQ).

Other useful oils are the tocopherols, particularly in combination with squalene. Where the oil phase of an emulsion includes a tocopherol, any of the α, β, γ, δ, ε or ξ tocopherols can be used, but α-tocopherols are preferred. D-α-tocopherol and DL-α-tocopherol can both be used. A preferred α-tocopherol is DL-α-tocopherol.

The oil in the emulsion may comprise a combination of oils e.g. squalene and at least one other oil. An oil combination comprising squalene and a tocopherol (e.g. DL-α-tocopherol) can be used. In some embodiments, however, an emulsion includes a single oil component.

The aqueous component of the emulsion can be plain water (e.g. w.f.i.) or can include further components e.g.

solutes. For instance, it may include salts to form a buffer e.g. citrate or phosphate salts, such as sodium salts. Typical buffers include: a phosphate buffer; a Tris buffer; a borate buffer; a succinate buffer; a histidine buffer; or a citrate buffer. A buffered aqueous phase is preferred, and buffers will typically be included in the 5-20 mM range.

In addition to the oil and aqueous components, an emulsion will generally include a surfactant, such as a non-ionic and/or a zwitterionic surfactant. Such surfactants include, but are not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy) polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether; and sorbitan esters (commonly known as the Spans), such as sorbitan trioleate (Span 85) and sorbitan monolaurate. Preferred surfactants for including in the emulsion are polysorbate 80 (Tween 80; polyoxyethylene sorbitan monooleate), sorbitan trioleate (Span 85), lecithin and/or octoxynol-9 (Triton X-100). Emulsions including polysorbate 80 are particularly preferred.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxy-polyethoxyethanol (Triton X-100) is also suitable. Another useful combination comprises laureth-9 plus a polyoxyethylene sorbitan ester and/or an octoxynol.

Surfactants can be classified by their 'HLB' (hydrophile/lipophile balance), where a HLB in the range 1-10 generally means that the surfactant is more soluble in oil than in water, and a HLB in the range 10-20 are more soluble in water than in oil. If multiple surfactants are used then it will be usual to include surfactants with HLB values which differ by at least 5.

Useful mixtures can comprise a surfactant with a HLB value in the range of 10-20 (e.g. polysorbate 80, with a HLB of 15.0) and a surfactant with a HLB value in the range of 1-10 (e.g. sorbitan trioleate, with a HLB of 1.8). A mixture of polysorbate 80 and sorbitan trioleate at a 1:1 weight ratio is useful.

Preferred amounts of total oil (% by volume) in the final emulsion are between 2-20% e.g. 5-15%, 6-14%, 7-13%, 8-12%, 4-5%. A squalene content of 4-6% is particularly useful.

Preferred amounts of surfactants (% by volume) in the final emulsion are between 0.001% and 8%, and ideally no more than 7% e.g. from 0.01-5% by volume. For example: polyoxyethylene sorbitan esters (such as polysorbate 80) 0.2 to 4%, in particular between 0.4-0.6%, between 0.42-0.5%, about 0.5% or between 1.5-2%, between 1.8-2.2%, between 1.9-2.1%, about 2%, or 0.85-0.95%, or about 1%, or about 1.8%; sorbitan esters (such as sorbitan trioleate) 0.02 to 2%, in particular about 0.5% or about 1%; octyl- or nonylphenoxy polyoxyethanols (such as Triton X-100) 0.001 to 0.1%, in particular 0.005 to 0.02%; polyoxyethylene ethers (such as laureth-9) 0.1 to 8%, preferably 0.1 to 10% and in particular 0.1 to 1% or about 0.5%. A total surfactant content of between 0.9-1.0% by volume or between 1.7-1.9% by volume is useful.

The absolute amounts of oil and surfactant, and their ratio, can be varied within wide limits while still forming an emulsion. A skilled person can easily vary the relative proportions of the components to obtain a desired emulsion, but a weight ratio of between 4:1 and 5:1 for oil and surfactant is typical (weight excess of oil).

An important parameter for ensuring immune stimulatory activity of an emulsion, particularly in large animals, is the oil droplet size (diameter). The most effective emulsions have a droplet size in the submicron range. Suitably the droplet sizes will be in the range 50-750 nm. Most usefully the average droplet size is less than 220 nm (e.g. less than 200 nm, less than 150 nm) as they can be subjected to filter sterilization. In some embodiments emulsions of the invention are filtered using a filter having a pore size of 0.22 μm or lower, which is typical for filter sterilization.

The average droplet size is usefully in the range of 80-180 nm. Ideally, at least 80% (by number) of the emulsion's oil droplets are less than 220 nm in diameter, and preferably at least 90%. These droplet sizes can conveniently be achieved by techniques such as microfluidisation (which propels streams of components through geometrically fixed channels at high pressure and high velocity, thereby achieving mixing and, for an emulsion, formation of small droplets). Apparatuses for determining the average droplet size in an emulsion, and the size distribution, are commercially available. These typically use the techniques of dynamic light scattering and/or single-particle optical sensing e.g. the Accusizer™ and Nicomp™ series of instruments available from Particle Sizing Systems (Santa Barbara, USA), or the Zetasizer™ instruments from Malvem Instruments (UK), or the Particle Size Distribution Analyzer instruments from Horiba (Kyoto, Japan). See also [21]. Dynamic light scattering (DLS) is the preferred method by which oil particle diameters are determined. The preferred method for defining the average oil particle diameter is a Z-average i.e. the intensity-weighted mean hydrodynamic size of the ensemble collection of droplets measured by DLS. The Z-average is derived from cumulants analysis of the measured correlation curve, wherein a single particle size (droplet diameter) is assumed and a single exponential fit is applied to the autocorrelation function. Thus, references herein to an average diameter should be taken as an intensity-weighted average, and ideally the Z-average.

Ideally, the distribution of droplet sizes (by number) has only one maximum i.e. there is a single population of droplets distributed around an average (mode), rather than having multiple maxima. Preferred emulsions have a polydispersity of <0.35 (PdI). Polydispersity is a measure of the width of the size distribution of particles, and is conventionally expressed as the polydispersity index (PdI). A polydispersity index of greater than 0.7 indicates that the sample has a very broad size distribution and a reported value of 0 means that size variation is absent, although values smaller than 0.05 are rarely seen. It is preferred for oil droplets within an emulsion of the invention to be of a relatively uniform size. Thus oil droplets in emulsions preferably have a PdI of less than 0.35 e.g. less than 0.3, 0.275, 0.25, 0.225, 0.2, 0.175, 0.15, 0.125, or even less than 0.1. PdI values are easily provided by the same instrumentation which measures droplet diameter (see above).

Usefully, the number of oil droplets having a diameter of >1.2 m in an oil-in-water emulsion of the invention is $5 \times 10^8$/mL or less, e.g., $5 \times 10^8$/mL or less, $5 \times 10^7$/mL or less, $5 \times 10^6$/mL or less, or $5 \times 10^5$/mL or less.

Emulsions with oil droplets having these size characteristics can conveniently be formed by microfluidising at least one oil, an aqueous component such as water, and at least one surfactant. A microfluidisation step can usefully be preceded by a step which mixes components first by using a homogenizer. Where a component includes more than one compound (e.g., two different oils in the oil component, two different surfactants in the surfactant component, etc.), these may be combined in various orders prior to emulsification, e.g., a first surfactant and an oil may be pre-mixed, to be combined with a mixture of a second surfactant and an aqueous component.

Emulsions of the invention may be prepared in accordance with the techniques variously disclosed in [22] to [24] (the complete contents of each of which are incorporated herein by reference).

Thus emulsification may involve formation of a first emulsion by homogenization, followed by microfluidization to provide a second emulsion. Components may be recirculated through the homonogenizer and/or the microfluidiser using 'type II' circulation [23], or a combination of 'type I' and 'type II' circulation. An inert atmosphere can be used during mixing. Temperature can be controlled around 40° C., for example, between about 35° C. and 45° C., e.g., about 35° C., about 36° C., about 37° C., about 38° C., about 38° C., about 40° C., about 41° C., about 42° C., about 43° C., about 44° C., and about 45° C. The emulsions can be filtered using a sterile asymmetric hydrophilic PES membrane. In some embodiments, the emulsions may be filtered using a sterile dual-layer (double-layer) 0.45 μm/0.22 μm asymmetric hydrophilic PES membrane filter.

Specific oil-in-water emulsions useful with the invention include, but are not limited to, the following, from which squalene-containing emulsions are preferred:

A submicron emulsion of squalene, polysorbate 80, and sorbitan trioleate. The emulsion may include citrate ions in the aqueous phase e.g. 10 mM sodium citrate buffer. The composition of the emulsion by volume can be about 4.5% squalene, about 0.5% polysorbate 80 and about 0.5% sorbitan trioleate. This adjuvant is known as 'MF59' [25-27], as described in more detail in Chapter 10 of [28] and chapter 12 of [29]. Concentrations of about 39 mg/mL squalene, about 4.7 mg/mL polysorbate 80, and about 4.7 mg/mL sorbitan trioleate are typical. A Z-average droplet size of between 155-185 nm is preferred, with a polydispersity of <0.2.

An emulsion comprising squalene, a tocopherol (in particular, DL-α-tocopherol), and polysorbate 80. The emulsion may include phosphate buffered saline. These emulsions may have by volume from 2 to 10% squalene, from 2 to 10% tocopherol and from 0.3 to 3% polysorbate 80, and the weight ratio of squalene:tocopherol is preferably <1 (e.g. 0.90) as this can provide a more stable emulsion. Squalene and polysorbate 80 may be present volume ratio of about 5:2 or at a weight ratio of about 11:5. Thus the three components (squalene, tocopherol, polysorbate 80) may be present at a weight ratio of 1068:1186:485 or around 55:61:25. One such emulsion ('AS03' [14]) includes 4.3% by weight squalene, 4.8% by weight tocopherol, and 2% by weight polysorbate 80. Concentrations of about 42.7 mg/mL squalene, about 47.4 mg/mL DL-α-tocopherol, and about 19.4 mg/mL polysorbate 80 are typical. A Z-average droplet size of between 140-170 nm is preferred. The emulsion may also include a 3-de-O-acylated monophosphoryl lipid A (3d MPL). Another useful emulsion of this type may comprise, per human dose, 0.5-10 mg squalene, 0.5-11 mg tocopherol, and 0.1-4 mg polysorbate 80 [30] e.g. in the ratios discussed above.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [31]. The emulsion may also include one or more of: alditol; a cryoprotective agent (e.g. a sugar, such as dodecylmaltoside and/or sucrose); and/or an alkylpolyglycoside. The emulsion may include a TLR4 agonist [32]. Such emulsions may be lyophilized. A preferred emulsion includes squalene, sorbitan oleate, polyoxyethylene cetostearyl ether and mannitol (e.g. 32.5% squalene, 4.82% sorbitan oleate, 6.18% polyoxyethylene cetostearyl ether and 6% mannitol; % s by weight), with an average droplet size below 150 nm. Concentrations of about 49.6 mg/mL squalene, about 7.6 mg/mL sorbitan oleate, and about 9.6 mg/mL polyoxyethylene cetostearyl ether, and 9.2 mg/mL mannitol are typical.

An emulsion comprising squalene, phosphatidylcholine (e.g. dipalmitoyl phosphatidylcholine; aka. lecithin), poloxamer 188 (e.g. Pluronic® F68), glycerol and an ammonium phosphate buffer [33], optionally also including an α-tocopherol ('SE').

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [34] (0.05-1% Thr-MDP, 5% squalane, 2.5% Pluronic L121 and 0.2% polysorbate 80). It can also be used without the Thr-MDP, as in the "AF" adjuvant [35](5% squalane, 1.25% Pluronic L121 and 0.2% polysorbate 80). Microfluidisation is preferred.

An emulsion of squalene, poloxamer 105 and Abil-Care [36]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% oil, 0.1-10% phospholipid, and 0.05-5% non-ionic surfactant. As described in [37], preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in [38], produced by addition of aliphatic amine to desacylsaponin via the carboxyl group of glucuronic acid), dimethyidioctadecylammonium bromide and/or N,N-dioctadecyl-N,N-bis (2-hydroxyethyl)propanediamine.

An emulsion in which a saponin (e.g. QuilA or QS21) and a sterol (e.g. a cholesterol) are associated as helical micelles [39].

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [40].

Thus any of these emulsions can be modified by adding retinoic acid, but the first three in the list are particularly preferred.

To make a vaccine for injection these emulsions will generally be mixed with an aqueous immunogen preparation. This mixing typically involves the emulsion in aqueous form with the immunogen in aqueous form at a 1:1 volume ratio, in which case the proportion of the emulsion's components will be halved in a final vaccine. For instance, an emulsion with 5% by volume squalene can be mixed at a 1:1 ratio with an antigen solution to give a vaccine with a final concentration of 2.5% by volume. Other mixing ratios are, of course, possible e.g. using a volume ratio of the two liquids for mixing between 5:1 and 1:5. Thus in a vaccine composition the concentrations of components of the emulsions noted above may be modified by dilution (e.g. by an integer, such as 2 or 3) in which their ratios stay the same.

Emulsions of the invention are ideally stored at between 2° C. and 8° C. They should not be frozen. They should ideally be kept out of direct light. In particular, squalene-containing emulsions and immunogenic composition, e.g. vaccines, of the invention should be protected to avoid photochemical breakdown of squalene. If emulsions are stored then this is preferably in an inert atmosphere e.g. $N_2$ or argon.

Immunogenic Compositions

Although it is possible to administer oil-in-water emulsion adjuvants on their own to patients (e.g. to provide an adjuvant effect for an antigen that has been separately administered to the patient), it is more usual to admix the adjuvant with an immunogenic composition, e.g. an antigen, prior to administration, to form an immunogenic composition, e.g., a vaccine. Mixing of emulsion and antigen may take place extemporaneously, at the time of use, or can take place during vaccine manufacture, prior to filling. The methods of the invention can be applied in both situations.

Thus a process of the invention may comprise a step of admixing an emulsion of the invention with an immunogen component. As an alternative, it may include a step of packaging the emulsion into a kit as a kit component together with an immunogen component.

Overall, therefore, the invention can be used when preparing mixed vaccines or when preparing kits including immunogen and adjuvant ready for mixing. Where mixing takes place during manufacture then the volumes of bulk antigen and emulsion that are mixed will typically be greater than 1 liter e.g. ≥5 liters, ≥10 liters, ≥20 liters, ≥50 liters, ≥100 liters, ≥250 liters, etc. Where mixing takes place at the point of use then the volumes that are mixed will typically be smaller than 1 milliliter e.g. ≤0.6 ml, ≤0.5 ml, ≤0.4 ml, ≤0.3 ml, ≤0.2 ml, etc. In both cases it is usual for substantially equal volumes of emulsion and immunogen solution/suspension to be mixed i.e. substantially 1:1 (e.g. between 1.1:1 and 1:1.1, preferably between 1.05:1 and 1:1.05, and more preferably between 1.025:1 and 1:1.025). In some embodiments, however, an excess of emulsion or an excess of antigen may be used [41]. Where an excess volume of one component is used, the excess will generally be at least 1.5:1 e.g. ≥2:1, ≥2.5:1, ≥3:1, ≥4:1, ≥5:1, etc.

Where antigen and adjuvant are presented as separate components within a kit, they are physically separate from each other within the kit, and this separation can be achieved in various ways. For instance, the components may be in separate containers, such as vials. The contents of two vials can then be mixed when needed e.g. by removing the contents of one vial and adding them to the other vial, or by separately removing the contents of both vials and mixing them in a third container.

In another arrangement, one of the kit components is in a syringe and the other is in a container such as a vial. The syringe can be used (e.g. with a needle) to insert its contents into the vial for mixing, and the mixture can then be withdrawn into the syringe. The mixed contents of the syringe can then be administered to a patient, typically through a new sterile needle. Packing one component in a syringe eliminates the need for using a separate syringe for patient administration.

In another preferred arrangement, the two kit components are held together but separately in the same syringe e.g. a dual-chamber syringe. When the syringe is actuated (e.g. during administration to a patient) then the contents of the two chambers are mixed. This arrangement avoids the need for a separate mixing step at time of use.

The contents of the various kit components will generally all be in liquid form. In some arrangements, a component (typically the antigen component rather than the emulsion component) is in dry form (e.g. in a lyophilized form), with the other component being in liquid form. The two components can be mixed in order to reactivate the dry component and give a liquid composition for administration to a patient. A lyophilized component will typically be located within a vial rather than a syringe. Dried components may include stabilizers such as lactose, sucrose or mannitol, as well as mixtures thereof e.g. lactose/sucrose mixtures, sucrose/mannitol mixtures, etc. One possible arrangement uses a liquid emulsion component in a pre-filled syringe and a lyophilized antigen component in a vial.

If vaccines contain components in addition to emulsion and antigen then these further components may be included in one these two kit components, or may be part of a third kit component.

Suitable containers for mixed vaccines of the invention, or for individual kit components, include vials and disposable syringes. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. In one embodiment, a vial has a butyl rubber stopper. The vial may include a single dose of vaccine/component, or it may include more than one dose (a 'multidose' vial) e.g. 10 doses. In one embodiment, a vial includes 10×0.25 ml doses of emulsion. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilized material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed.

Where a composition/component is packaged into a syringe, the syringe will not normally have a needle attached to it, although a separate needle may be supplied with the syringe for assembly and use. Safety needles are preferred. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Syringes with an internal volume of up to 5 ml are typical for use with the invention.

Needles useful for intramuscular injection are generally 16-38 mm (5/8"-1.5") long, with 19-27 gauge (outer diameter from 0.4-1 mm). Injectable compositions of the invention should be suitable for administration by hand from a syringe via such needles. Within these ranges, shorter needles and higher gauges are generally for pediatric use.

The emulsion may be diluted with a buffer prior to packaging into a vial or a syringe. Typical buffers include: a phosphate buffer; a Tris buffer; a borate buffer; a succinate buffer; a histidine buffer; or a citrate buffer. Dilution can reduce the concentration of the adjuvant's components while retaining their relative proportions e.g. to provide a "half-strength" adjuvant.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

Various antigens can be used with oil-in-water emulsions, including but not limited to: viral antigens, such as viral surface proteins; bacterial antigens, such as protein and/or saccharide antigens; fungal antigens; parasite antigens; and tumor antigens. Thus the invention can be used for adjuvanting immunogens from various sources. The immunogen may be from a bacterium, a virus, a fungus, or a parasite. Thus a vaccine may protect against disease caused by a bacterium, a virus, a fungus, and/or a parasite.

Typical bacteria for use with the invention include, but are not limited to:
  Bordetella, such as *B. pertussis*.
  Clostridia, such as *C. tetani* and *C. botulinum*
  Corynebacteria, such as *C. diphtheriae*.
  Pasteurella, such as *Haemophilus influenzae*.
  Mycobacteria, such as *M. tuberculossi, M. bovis* and the attenuated *Bacillus Calmette Guerin*.
  Neisseria, such as *N. meningitidis* and *N. gonorrhoeae*.
  Salmonella, such as *S. typhi, S. paratyphi, S. typhimurium, S. enteritidis*.
  Streptococci, such as *S. pneumoniae* (pneumococcus), *S. agalactiae* and *S. pyogenes*.

Typical viruses for use with the invention include, but are not limited to:
  Orthomyxovirus, such as an influenza A, B or C virus. Influenza A or B viruses may be interpandemic (annual/seasonal) strains, or from strains with the potential to cause a pandemic outbreak (i.e., influenza strains with new hemagglutinin compared to a hemagglutinin in currently circulating strains, or influenza strains which are pathogenic in avian subjects and have the potential to be transmitted horizontally in the human population, or influenza strains which are pathogenic to humans). Depending on the particular season and on the nature of the strain, an influenza A virus may be derived from one or more of the following hemagglutinin subtypes: H1, H2, H3, H4, H5, H6, H7, H8, H9, H10, H11, H12, H13, H14, H15 or H16. Vaccine may include hemagglutinin from one or more (e.g. 1, 2, 3, 4 or more) influenza virus strains, including influenza A virus and/or influenza B virus, e.g. a monovalent A/H5N1 or A/H1N1 vaccine, or a trivalent A/H1N1+A/H3N2+B vaccine, or a tetravalent a trivalent A/H1N1+A/H3N2+B/Yamagata+B/Victoria vaccine. Unit doses of influenza vaccine are typically standardized by reference to hemagglutinin (HA) content, typically measured by SRID. Existing vaccines typically contain about 15 µg of HA per strain, although lower doses can be used. Fractional doses such as ½ (i.e. 7.5 µg HA per strain), ¼ and ⅛ have been used [42,43], as have higher doses (e.g. 3× or 9× doses [44,45]). Thus vaccines may include between 0.1 and 150 µg of HA per influenza strain, preferably between 0.1 and 50 µg e.g. 0.1-20 µg, 0.1-15 µg, 0.1-10 µg, 0.1-7.5 µg, 0.5-5 µg, etc. Particular doses include e.g. about 15, about 10, about 7.5, about 5, about 3.8, about 3.75, about 1.9, about 1.5, etc. per strain.
  Paramyxoviridae viruses, such as Pneumoviruses (RSV), Paramyxoviruses (PIV) and Morbilliviruses (Measles).
  Pneumovirus or metapneumovirus, for example respiratory syncytial virus (RSV), Bovine respiratory syncytial virus, Pneumonia virus of mice, and Turkey rhinotracheitis virus. Preferably, the Pneumovirus is RSV or human metapneumovirus (HMPV).
  Paramyxovirus, such as Parainfluenza virus (PIV) type 1, 2, 3 or 4, Mumps, Sendai viruses, Simian virus 5, Bovine parainfluenza virus and Newcastle disease virus. Preferably, the Paramyxovirus is PIV or Mumps.
  Picornavirus, such as Enteroviruses, Rhinoviruses, Hepamavirus, Cardioviruses and Aphthoviruses. Enteroviruses include Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. Preferably, the Enterovirus is poliovirus e.g. a type 1 strain such as Mahoney or Brunenders, a type 2 strain such as MEF-I, or a type 3 strain such as Saukett. An example of a Hepamaviruses (also named Hepatoviruses) is Hepatitis A virus.
  Togavirus, such as a Rubivirus, an Alphavirus, or an Arterivirus. Rubiviruses, such as Rubella virus, are preferred. Useful alphaviruses for inactivation include aquatic alphaviruses, such as salmon pancreas disease virus and sleeping disease virus.
  Flavivirus, such as Tick-borne encephalitis (TBE), Dengue (types 1, 2, 3 or 4), Yellow Fever, Japanese encephalitis, West Nile encephalitis, St. Louis encephalitis, Russian spring-summer encephalitis, Powassan encephalitis.

Hepatitis C virus (HCV).

Pestivirus, such as Bovine viral diarrhea (BVDV), Classical swine fever (CSFV) or Border disease (BDV).

Hepadnavirus, such as Hepatitis B virus. Hepatitis B virus surface antigen is preferably obtained by recombinant DNA methods e.g. after expression in a *S. cerevisiae* yeast. Unlike native viral HBsAg, the recombinant yeast-expressed antigen is non-glycosylated. It can be in the form of substantially-spherical particles (average diameter of about 20 nm), including a lipid matrix comprising phospholipids. Unlike native HBsAg particles, the yeast-expressed particles may include phosphatidylinositol. The HBsAg may be from any of subtypes ayw1, ayw2, ayw3, ayw4, ayr, adw2, adw4, adrq– and adrq+.

Rhabdovirus, such as a Lyssavirus (e.g. a rabies virus) and Vesiculovirus (VSV).

Caliciviridae, such as Norwalk virus, and Norwalk-like Viruses, such as Hawaii Virus and Snow Mountain Virus, and Vesivirus, such as Vesicular Exanthema of Swine Virus.

Coronavirus, such as a SARS, Human respiratory coronavirus, Avian infectious bronchitis (IBV), Mouse hepatitis virus (MHV), and Porcine transmissible gastroenteritis virus (TGEV).

Retrovirus, such as an Oncovirus, a Lentivirus or a Spumavirus. An oncovirus may be HTLV-1, HTLV-2 or HTLV-3. A lentivirus may be SIV, HIV-1 or HIV-2.

Reovirus, such as an Orthoreovirus, a Rotavirus, an Orbivirus, or a Coltivirus.

Parvovirus, such as Parvovirus B19, or Bocavirus.

Human Herpesvirus, such as Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8).

Papovaviruses, such as Papillomaviruses and Polyomaviruses. Papillomaviruses include HPV serotypes 1, 2, 4, 5, 6, 8, 11, 13, 16, 18, 31, 33, 35, 39, 41, 42, 47, 51, 57, 58, 63 and 65.

Adenoviridae, including any of human adenoviruses A, B, C, D, E, F or G.

The invention is ideal for adjuvanting vaccines for viruses, and in particular viruses where the vaccine antigen is a viral surface glycoprotein.

As mentioned above, a solution or suspension of the immunogen will normally be mixed with the emulsion e.g. at a 1:1 volume ratio. This mixing can either be performed by a vaccine manufacturer, prior to filling, or can be performed at the point of use, by a healthcare worker.

An immunogenic composition of the invention may include components in addition to the emulsion and an optional antigen.

The composition may include a preservative such as thiomersal or 2-phenoxyethanol. It is preferred, however, that the vaccine should be substantially free from (i.e. less than 5 µg/ml) mercurial material e.g. thiomersal-free [46, 47]. Vaccines and components containing no mercury are more preferred. Preservative-free vaccines are also useful.

In some embodiments (cf. [48]) an emulsion, or an immunogenic composition, e.g., an emulsion-containing vaccine, does not include one or more of: (i) oleic acid, (ii) butylated hydroxytoluene; (iii) lecithin, and in particular soy lecithin; (iv) medium-chain triglycerides; and/or (v) soybean oil. Medium-chain triglycerides are a mixture of triglycerides of saturated fatty acids, mainly of caprylic acid and capric acid, and can include a minimum of 95% by weight of C8 and C10 saturated fatty acids. They are usually obtained from coconut oil or palm kernel oil.

In some embodiments (cf. [49]) an emulsion, or an immunogenic composition, e.g., an emulsion-containing vaccine, does not include one or more of: (i) oleic acid; (ii) butylated hydroxytoluene; (iii) lecithin, and in particular soy lecithin; (iv) medium-chain triglycerides; (v) soybean oil and/or (vi) cetyl palmitate.

The pH of a composition will generally be between 5.0 and 8.1, and more typically between 6.0 and 8.0 e.g. between 6.5 and 7.5. A process of the invention may therefore include a step of adjusting the pH of the vaccine prior to packaging. The composition may include a buffer.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunization, or may include material for multiple immunizations (i.e. a 'multidose' kit). The inclusion of a preservative is preferred in multidose arrangements.

Vaccines are typically administered in a dosage volume of about 0.5 ml, although a half dose (i.e. about 0.25 ml) may be administered to children.

Methods of Treatment, and Administration of the Vaccine

Emulsions and immunogenic compositions of the invention can be delivered to a subject via injection. Thus the invention provides a method of raising an immune response in a subject, comprising the step of administering an emulsion or an immunogenic composition of the invention to the subject e.g. by intramuscular injection.

The invention also provides an emulsion or immunogenic composition of the invention for use in a method of vaccinating a subject. The invention also provides the use of an emulsion of the invention in the manufacture of a medicament for raising an immune response in a subject. Similarly, the invention provides the use of an oil, a surfactant, an aqueous component, and RA in the manufacture of a medicament for raising an immune response in a subject.

Kits, emulsions and compositions of the invention are also provided for use as medicaments.

The immune response raised by these methods and uses will generally include an antibody response, preferably a protective antibody response e.g. via serum IgG. Advantageously, the inclusion of RA means that the immune response can include a mucosal immune response, such as mucosal IgA, thereby enhancing protection against mucosal challenges. The immune response may provide immunogen-specific $CD4^+$ and $CD8^+$ T cells.

The invention is suitable for administering vaccines to human or non-human animal subjects. Vaccines prepared according to the invention may be used to treat both children and adults. Because RA may sometimes be embryotoxic, however, it is preferred that the invention is not used for pregnant women, and in some embodiments not for women of childbearing age.

As an alternative to intramuscular injection (e.g. into the arm or leg) or subcutaneous injection, compositions of the invention can be administered in any other suitable way, including, but not limited to: intranasal [50-52], oral [53], intradermal [54,55], transdermal [56], etc.

Vaccines of the invention may be administered to patients at substantially the same time as (e.g. during the same medical consultation or visit to a healthcare professional) other vaccines.

Treatment can be by a single dose schedule or a multiple dose schedule. Multiple doses may be used in a primary immunisation schedule and/or in a booster immunisation schedule. Multiple doses can be administered at least 1 week apart (e.g. about 2 weeks, about 3 weeks, about 4 weeks, about 6 weeks, about 8 weeks, about 10 weeks, about 12 weeks, about 16 weeks, etc.).

General

Throughout the specification, including the claims, where the context permits, the term "comprising" and variants thereof such as "comprises" are to be interpreted as including the stated element (e.g., integer) or elements (e.g., integers) without necessarily excluding any other elements (e.g., integers). Thus a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention. In some embodiments, "a composition that is substantially free of a component" may include such a composition with a residual amount of the component, wherein the residual amount is (i) below reliable detection levels by suitable or art-accepted measurement means; and/or (ii) the residual amount does not adversely affect an intended purpose of the composition.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

EXAMPLES

This invention is further illustrated by the following examples, which should not be construed as limiting.

Oil-in-Water Emulsions for Up-Regulating CCR9 on Antigen-Specific T Cells

CCR9 is a key homing receptor involved in regulating effector T-cell migration to intestinal mucosa. MF59 and/or retinoic acid were tested for their effect on expression of CCR9 on $CD4^+$ and $CD8^+$ T-cells. A negative control was also tested.

Figure 1:
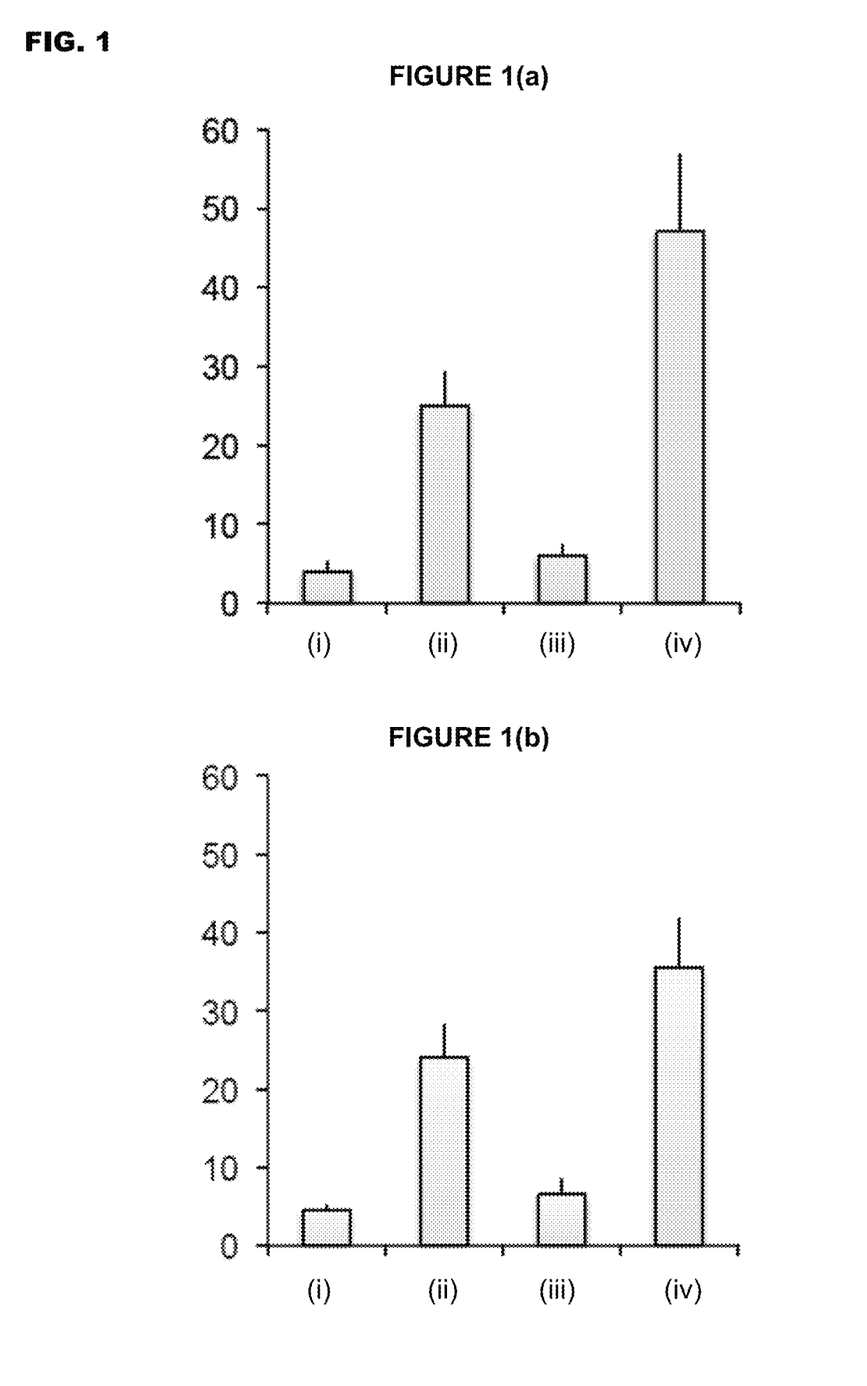
FIG. 1 shows the proportion of (a) $CD4^+$ and (b) $CD8^+$ antigen-specific T cells after administration of (i) medium alone (ii) retinoic acid (iii) MF59 or (iv) retinoic acid and MF59. The y-axis shows the % of CCR9+ cells.

Antigen-presenting cells isolated from bone marrow were cultured with $CD4^+$ or $CD8^+$ antigen-specific T cells from transgenic mice with ovalbumin-specific T-cells (DO-11.10 or OT-I mice) in the presence of ovalbumin and adjuvant. FIG. 1 shows the proportion of (a) $CD4^+$ and (b) $CD8^+$ antigen-specific T cells which are CCR9-positive, with the highest proportion being seen when MF59 and retinoic acid were both administered (i.e. group (iv) in the FIGURES).

Adoptive T-Cell Transfer

Reference [57] describes experimental protocols for studying the homing of T-cells in mice who receive retinoic acid. In brief, T-cells specific for test antigens (in the present case, ovalbumin) are adoptively transferred into mice and their behaviour in response to specific treatments is studied. This general experimental procedure was used to assess the effect of MF59 and retinoic acid on CCR9 expression in T-cells, and on their in vivo migration.

Mice were injected intravenously with $2 \times 10^6$ $CD4^+$ T-cells which react to ovalbumin peptides (DO-11.10 cells). These cells were labelled with CFSE before being administered. At around the same time they were given either retinoic acid or a plain vehicle. The next day they received MF59-adjuvanted ovalbumin, and the next day they again received RA or plain vehicle, plus fingolimod (which blocks the egress of lymphocytes from lymph nodes). A few days later their draining lymph nodes were drained and $CD4^+$ T-cells expressing the DO-11.10 T-cell receptor were tested for CCR9 expression by FACS. The CFSE label was used to trace cell proliferation.

CFSE labelling confirmed that T cells proliferated in mice receiving MF59, with no real difference between mice receiving RA or vehicle. In relation to CCR9 expression, however, a big difference was seen: in the mice who had received MF59 and the plain vehicle CCR9 expression was essentially the same as seen in naïve mice, but in the mice who had received retinoic acid the number of CCR9-positive cells was about 5× higher.

In separate experiments a similar protocol was used, but without fingolimod administration, and antigen-specific $CD4^+$ T-cells were assessed in both the draining lymph nodes and lungs 7 days after T-cells cells were injected. In both of the MF59-treated groups the proportion of ovalbumin-specific T-cells in the draining lymph nodes was essentially the same, but in lungs the levels were about twice as high for animals who received retinoic acid. Thus retinoic acid did not cause a general change in T-cell responses, but it did increase their migration towards mucosal tissues.

Mucosal Antibody Responses

To assess antibody responses mice were injected with 3 doses of either ovalbumin or H56 (a malaria antigen) on days 0, 21, and 42, adjuvanted with MF59. The day before and after each immunization one group of mice were given retinoic acid whereas control mice received a plain vehicle instead. Serum IgG and vaginal wash IgA antibody responses were assessed at day 56. IgA-secreting cells were also measured in the bone marrow.

Serum IgG titres against ovalbumin or H56 were essentially the same in mice who received retinoic acid or the plain vehicle. In contrast, antigen-specific IgA titres in vaginal washes were essentially zero in mice who received plain vehicle, but were about 1250 in mice who had received retinoic acid. Moreover, the proportion of IgA-secreting cells was much higher in mice who had received retinoic acid: about 7× higher for ovalbumin, and around 12× higher for H56.

Formation of Emulsions Including Retinoic Acid

Three oil-in-water emulsions (A, B, C) were made with or without all-trans retinoic acid in the oil phase. Emulsion A is similar to 'MF59' [13]; emulsion B is similar to 'AS03' [14]; and emulsion C is similar to 'SE' [aka. Stable Emulsion of Immune Design—see above].

The components for test batches of each emulsion were as follows, with 60 mg retinoic acid (RA) also being included in the oil phase where appropriate:
- (A) oil phase: 100 mg Span 85, 860 mg squalene; aqueous phase: 100 mg Tween 80, 19.5 ml 10 mM citrate buffer.
- (B) oil phase: 855.2 mg squalene, 948.8 mg±-α-tocopherol; aqueous phase: 388.8 mg Tween 80, 19.5 ml 1× phosphate-buffered saline.
- (C) oil phase: 380 mg lecithin, 2.02 mL squalene, 12 mg±-α-tocopherol; aqueous phase: 454 mg glycerol, 18 mg Pluronic F68, 2 mL 250 mM ammonium phosphate pH 5.1, 15.64 ml ultrapure water.

Where retinoic acid did not dissolve in the oil phase it was first dissolved in dichloromethane (DCM) at 5 mg/mL and then added to the oil. The DCM was then allowed to evaporate at room temperature.

To form the emulsions, the oil and aqueous phases were homogenised for about 2 minutes, and then up to 32 churns through a microfluidiser were used. 12 passes at 30,000 psi was generally fine.

The emulsions without retinoic acid formed easily, and had the expected milky visual appearance. They were easily filtered. The emulsions with retinoic acid were yellow in colour and were more difficult to filter. The colour of emulsion $B^{+RA}$ changed from yellow to off-white after filtration. Precipitates were observed in emulsion $A^{+RA}$. Emulsion $C^{RA}$ was very difficult to filter.

CONCLUSIONS

MF59 in combination with retinoic acid (RA) induces expression of mucosal homing receptors on antigen-specific T lymphocytes in vitro, and also in vivo in draining lymph nodes.

Antigen-specific T lymphocytes are able to reach mucosal compartments after immunisation in the presence of retinoic acid.

Systemic and mucosal antigen-specific antibody responses are induced following systemic immunization with an oil-in-water emulsion adjuvant in the presence of retinoic acid.

Thus mucosal homing capacity and mucosal antigen-specific responses induced by oil-in-water emulsion adjuvants can be improved by including retinoic acid. Such emulsions can be made using the methods disclosed herein.

It will be understood that the invention has been described by way of example only and modifications may be made whilst remaining within the scope and spirit of the invention.

REFERENCES

[1] Lisulo et al. (2013) Clin Exp Immunol 175:468-75.
[2] Ma et al. (2005) J Immunol 174:7961-69.
[3] Ma & Ross (2005) PNAS USA 102:13556-61.
[4] Tan et al. (2011) J Virol 85:8316-27.
[5] Kusmartsev et al. (2003) Cancer Res 63:4441-49.
[6] U.S. Pat. No. 6,461,622.
[7] Simoni et al. (2001) Pure Appl. Chem. 73:1437-44.
[8] Alvarez et al. (2004) Bioorg Medic Chem Lett 14:6117-22.
[9] Muccio et al. (1998) J Med Chem 41:1679-87.
[10] Kagechika (2002) Curr Med Chem. 9:591-608.
[11] Le Doze et al. (2000) Drug Metab Dispos 28:205-11.
[12] Sandberg et al. (1994) Drug Metab Dispos 22:154-60.
[13] WO90/14837.
[14] Garçon et al. (2012) Expert Rev Vaccines 11:349-66.
[15] WO2010/023551
[16] Brito et al. (2011) Vaccine 29:6262-6268.
[17] WO94/26683.
[18] He et al. (2002) J Agric Food Chem 50:368-72.
[19] WO2011/141819
[20] U.S. Pat. No. 8,092,813.
[21] Light Scattering from Polymer Solutions and Nanoparticle Dispersions (W. Schartl), 2007. ISBN: 978-3-540-71950-2.
[22] WO2011/067669
[23] WO2011/067673
[24] WO2011/067672
[25] WO90/14837.
[26] Podda & Del Giudice (2003) Expert Rev Vaccines 2:197-203.
[27] Podda (2001) Vaccine 19: 2673-2680.
[28] Vaccine Design: The Subunit and Adjuvant Approach (eds. Powell & Newman) Plenum Press 1995 (ISBN 0-306-44867-X).
[29] Vaccine Adjuvants: Preparation Methods and Research Protocols (Volume 42 of Methods in Molecular Medicine series). ISBN: 1-59259-083-7. Ed. O'Hagan.
[30] WO2008/043774.
[31] US-2007/014805.
[32] US-2007/0191314.
[33] Fox et al. (2013) Vaccine 31:1633-1640.
[34] Allison & Byars (1992) Res Immunol 143:519-25.
[35] Hariharan et al. (1995) Cancer Res 55:3486-9.
[36] Suli et al. (2004) Vaccine 22(25-26):3464-9.
[37] WO95/11700.
[38] U.S. Pat. No. 6,080,725.
[39] WO2005/097181.
[40] WO2006/113373.
[41] WO2007/052155.
[42] WO01/22992.
[43] Hehme et al. (2004) Virus Res. 103(1-2):163-71.
[44] Treanor et al. (1996) J Infect Dis 173:1467-70.
[45] Keitel et al. (1996) Clin Diagn Lab Immunol 3:507-10.
[46] Banzhoff (2000) Immunology Letters 71:91-96.
[47] WO02/097072.
[48] Chinsriwongkul et al. (2010) PDA J Pharm Sci Tech 64:113-23.
[49] Chinsriwongkul et al. (2011) AAPS Phar Sci Tech DOI: 10.1208/s12249-011-9733-8.
[50] Greenbaum et al. (2004) Vaccine 22:2566-77.
[51] Zurbriggen et al. (2003) Expert Rev Vaccines 2:295-304.
[52] Piascik (2003) J Am Pharm Assoc (Wash DC). 43:728-30.
[53] Mann et al. (2004) Vaccine 22:2425-9.
[54] Halperin et al. (1979) Am J Public Health 69:1247-50.
[55] Herbert et al. (1979) J Infect Dis 140:234-8.
[56] Chen et al. (2003) Vaccine 21:2830-6.
[57] Hammerschmidt et al. (2011) J Clin Invest 121:3051-61.

The invention claimed is:

1. An oil-in-water emulsion including squalene; polysorbate 80; sorbitan trioleate and retinoic acid, wherein at least 80% (by number) of the emulsion's oil droplets are less than 220 nm in diameter and wherein the oil-in-water emulsion has 4-6% by volume squalene; 0.4-0.6% by volume polysorbate 80; 0.5% ±0.05 by volume sorbitan trioleate; and the retinoic acid is present at a concentration between 2 µg/mL to 2 mg/mL.

2. The oil-in-water emulsion of claim 1, wherein the emulsion is injectable.

3. An immunogenic composition comprising (i) the oil-in-water emulsion of claim 1, and (ii) at least one immunogen.

4. The oil-in-water emulsion of claim 1, wherein the retinoic acid is all-trans retinoic acid.

5. The oil-in-water emulsion of claim 1, wherein the emulsion does not contain one or more of oleic acid butylated hydroxytoluene, lecithin, medium-chain triglycerides, soybean oil, and/or cetyl palmitate.

6. The immunogenic composition of claim 3, wherein the retinoic acid is all-trans retinoic acid.

* * * * *